United States Patent [19]

Takematsu et al.

[11] 4,385,927
[45] May 31, 1983

[54] BENZAMIDE DERIVATIVES AND HERBICIDAL COMPOSITION CONTAINING THE SAME

[75] Inventors: Tetsuo Takematsu; Masaaki Hoya, both of Utsunomiya; Toshitaka Kaneshiki, Tokyo, all of Japan

[73] Assignee: Hodogaya Chemical Co., Ltd., Tokyo, Japan

[21] Appl. No.: 198,968

[22] Filed: Oct. 20, 1980

[30] Foreign Application Priority Data

Nov. 20, 1979 [JP] Japan .................................. 54-149460

[51] Int. Cl.³ .................... A01N 37/22; C07C 103/76; C07C 103/78
[52] U.S. Cl. .................................... 71/118; 564/162; 564/184
[58] Field of Search .................... 71/118; 564/162, 184

[56] References Cited

U.S. PATENT DOCUMENTS 4,123,554 10/1978 Kawada et al. ...................... 564/184
4,284,813 8/1981 Takematsu et al. .................. 71/118

*Primary Examiner*—Catherine L. Mills
*Attorney, Agent, or Firm*—Oblon, Fisher, Spivak, McClelland & Maier

[57] ABSTRACT

A herbicidal composition comprises a novel compound of benzamide derivative having the formula

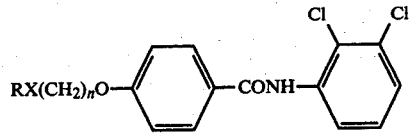

wherein R represents a $C_1-C_8$ alkyl group; X represents oxygen or sulfur atom and n is an integer of 1 or 2.

4 Claims, No Drawings

BENZAMIDE DERIVATIVES AND HERBICIDAL COMPOSITION CONTAINING THE SAME

BACKGROUND OF THE INVENTION

1. Field of the Invention

The present invention relates to novel benzamide derivatives and herbicidal compositions containing the benzamide derivative.

2. Description of the Prior Arts

Recently, many herbicides have been proposed and practically used to contribute for elimination of agricultural labour works.

Thus, various problems on herbicidal effects and safety of the herbicides have been found in the practical applications.

It has been required to find improved herbicides which have no adverse effect to the object plants and effective to noxious weeds in a small dose of the active ingredient and significantly safe without any environmental pollution.

The inventors have synthesized various benzamides so as to find satisfactory herbicides and have studied herbicidal effects thereof, and the present invention has been attained.

SUMMARY OF THE INVENTION

It is an object of the present invention to provide specific benzamide derivatives and herbicidal compositions containing the same as an active ingredient.

The foregoing and other objects of the present invention have been attained by providing novel benzamide derivatives having the formula

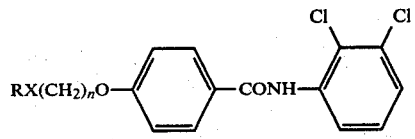

wherein R represents a $C_1$-$C_8$ alkyl group, X represents oxygen or sulfur atom; n is an integer of 1 or 2.

The herbicidal composition of the present invention comprises the novel benzamide derivative as an active ingredient and an adjuvant.

DETAILED DESCRIPTION OF THE PREFERRED EMBODIMENTS

The typical novel benzamide derivatives of the present invention include as follows.

TABLE 1

| Comp. No. | | Melting point (°C.) |
|---|---|---|
| 1 | 4-Methoxymethoxy-N—(2,3-dichlorophenyl)-benzamide | 109–111 |
| 2 | 4-Ethoxymethoxy-N—(2,3-dichlorophenyl)-benzamide | 87–88.5 |
| 3 | 4-n-Propoxymethoxy-N—(2,3-dichlorophenyl)-benzamide | 68.5–70.5 |
| 4 | 4-n-Butoxymethoxy-N—(2,3-dichlorophenyl)-benzamide | 70–71 |
| 5 | 4-(2-Methoxyethoxy)-N—(2,3-dichlorophenyl)-benzamide | 122–125 |
| 6 | 4-(2-Ethoxyethoxy)-N—(2,3-dichlorophenyl)-benzamide | 121.2–122 |
| 7 | 4-(2-n-Propoxyethoxy)-N—(2,3-dichlorophenyl)-benzamide | 98–100 |
| 8 | 4-(2-n-Butoxyethoxy)-N—(2,3-dichlorophenyl)-benzamide | 70–72 |

TABLE 1-continued

| Comp. No. | | Melting point (°C.) |
|---|---|---|
| 9 | 4-Methylthiomethoxy-N—(2,3-dichlorophenyl)-benzamide | 113–115 |
| 10 | 4-Ethylthiomethoxy-N—(2,3-dichlorophenyl)-benzamide | 89.5–91 |
| 11 | 4-n-Butylthiomethoxy-N—(2,3-dichlorophenyl)-benzamide | 58.5–60.5 |
| 12 | 4-(2-Methylthioethoxy)-N—(2,3-dichlorophenyl)-benzamide | 121.5–122.5 |
| 13 | 4-(2-Ethylthioethoxy)-N—(2,3-dichlorophenyl)-benzamide | 111–112 |

The benzamide derivatives of the present invention can be produced by the following process.

The benzamide derivatives can be produced by reacting 2,3-dichloroaniline with the corresponding benzoyl chloride derivative or benzoic acid ester derivative

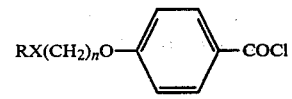

or

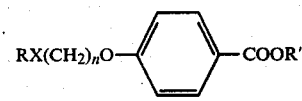

(R' represents a moiety of the ester) in the presence of a base in an organic solvent.

When the benzoyl chloride derivative is used, an organic or inorganic base such as alkali metal hydroxides and carbonates and pyridine and triethylamine can be used. The solvent can be any inert solvent such as acetone, toluene and dioxane. When the benzoic acid ester derivative is used, a special base such as sodium hydride or sodium methoxide is preferably used.

The solvent is preferably a polar solvent such as dimethylsulfoxide.

The benzamide derivatives can be produced by reacting 4-hydroxy-N-(2,3-dichlorophenyl)-benzamide

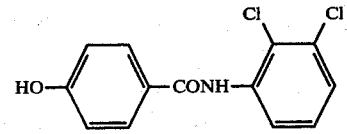

with the corresponding alkoxyalkyl halide or alkylthioalkyl halide

(Hal represents a halogen atom) in the presence of a base in an organic solvent.

An alkali metal salt of 4-hydroxy-N-(2,3-dichlorophenyl)benzamide can be used without using a base since it is the reaction product of the base. Potassium salt of 4-hydroxy-N-(2,3-dichlorophenyl)-benzamide is preferably used in the latter case.

The base can be inorganic and organic bases such as alkali metal hydroxides and carbonates and pyridine and triethylamine.

The solvent can be inert organic solvents such as acetone toluene, dioxane and N,N-dimethylformamide.

A molar ratio of the corresponding benzoyl chloride derivative or benzoic acid ester derivative to 2,3-dichloroaniline is usually in a range of 1 to 4 preferably 1 to 2.

The reaction temperature can be in a range of room temperature to a refluxing temperature.

The solvent can be aromatic hydrocarbons such as benzene, toluene and xylene and halohydrocarbons such as methylenechloride, chloroform and carbon tetrachloride, ketones such as acetone and ethers such as tetrahydrofuran and dioxane and polar solvents such as N,N-dimethylformamide and dimethylsulfoxide. An amount of the solvent is preferably in a range of 1 to 10 times by weight and preferably 2 to 5 times by weight of the total reactants.

A molar ratio of the corresponding benzoyl chloride derivative or benzoic acid ester derivative to the base is usually in a range of 1 to 6 preferably 1 to 2.

A molar ratio of the corresponding alkoxyalkyl halide or alkylthioalkyl halide to 4-hydroxy-N-(2,3-dichlorophenyl)-benzamide is usually in a range of 1 to 4 preferably 1 to 2.

The reaction temperature can be in a range of 0° C. to a refluxing temperature.

The solvent can be aromatic hydrocarbons such as benzene, toluene and xylene and halohydrocarbons such as methylenechloride, chloroform and carbon tetrachloride, ketones such as acetone and ethers such as tetrahydrofuran and dioxane and polar solvents such as N,N-dimethylformamide and dimethylsulfoxide. An amount of the solvent is preferably in a range of 1 to 10 times by weight and preferably 2 to 5 times by weight of the total reactants.

A molar ratio of the corresponding alkoxyalkyl halide or alkylthioalkyl halide to the base is usually in a range of 1 to 6 preferably 1 to 3.

Typical examples for preparations of the compounds will be illustrated.

Preparation 1: (Compound No. 6)

A mixture of 7.2 g. of p-ethoxyethoxy benzoic acid, 50 ml. of dioxane and 12.2 g. of thionyl chloride was refluxed at 70° to 80° C. for 2 hours. After the reaction, excess of thionyl chloride and the solvent were recovered by a rotary evaporator to obtain a crude p-ethoxyethoxybenzoic chloride as a residue. The crude p-ethoxyethoxybenzoic acid chloride was dissolved in 70 ml. of acetone and then, a mixture of 6.6 g. of 2,3-dichloroaniline and 4.1 g. of triethylamine was added dropwise with stirring at room temperature during 30 minutes. After the addition, the mixture was stirred at the same temperature for 2 hours. After the reaction, the reaction mixture was poured into 300 ml. of 2% hydrochloric acid and the resulting precipitate was separated by a filtration. The resulting crude product was recrystallized from toluene to obtain 9.0 g. of 4-(2-ethoxyethoxy)-N-(2,3-dichlorophenyl)-benzamide. The yield was 74.4 g. The compound had a melting point of 121.2° to 122° C.

Preparation 2: (Compound No. 4)

Into 20 ml. of toluene, 2.38 g. of methyl p-n-butoxymethoxybenzoate and 1.64 g. of 2,3-dichloroaniline were dissolved and 1.62 g. of sodium methoxide was added to the solution. The mixture was stirred at 105° to 115° C. for 4 hours. After the reaction, the reaction mixture was cooled to room temperature and the reaction mixture was washed for two times with 20 ml. of water and then was dehydrated over anhydrous sodium sulfate and then, toluene was recovered by a rotary evaporator to obtain an oily product. The oily product was crystallized from methanol to obtain 1.36 g. of 4-n-butoxymethoxy-N-(2,3-dichlorophenyl)-benzamide as the object product. The yield was 36.8% and a melting point of the product was in a range of 70.0° to 71.0° C.

Preparation No. 3: (Compound No. 12)

Into 30 ml. of N,N-dimethylformamide, 5.64 g. of 4-hydroxy-N-(2,3-dichlorophenyl)-benzamide, 3.32 g. of 2-chloroethyl methylsulfide and 8.29 g. of potassium carbonate were dispersed and the mixture was stirred at 100° to 110° C. during 6 hours. After the reaction, the reaction mixture was poured into 300 ml. of 2% hydrochloric acid. The resulting precipitate was separated by a filtration and the resulting crude product was recrystallized from ethanol to obtain 5.05 g. of 4-(2-methylthioethoxy)-N-(2,3-dichlorophenyl)-benzamide as the object product. The yield was 70.9% and the melting point of the product was 121.5° to 122.5° C.

Preparation No. 4: (Compound No. 5)

In accordance with the process of Preparation 3, except using 4.17 g. of 2-bromoethyl methyl ether instead of 2-chloroethyl methylsulfide, a reaction was carried out to obtain 4.45 g. of 4-(2-methoxyethoxy)-N-(2,3-dichlorophenyl)-benzamide having a melting point of 122° to 125° C. as the object product. The yield was 65.4%.

Preparation No. 5: (Compound No. 7)

In accordance with the process of Preparation 3, except using 5.01 g. of 2-bromoethyl n-propyl ether instead of 2-chloroethyl methylsufide, a reaction was carried out to obtain 5.16 g. of 4-(2-n-propoxyethoxy)-N-(2,3-dichlorophenyl)-benzamide having a melting point of 98° to 100° C. as the object product. The yield was 70.1%.

Preparation No. 6: (Compound No. 8)

In accordance with the process of Preparation 3, except using 5.43 g. of 2-bromoethyl n-butyl ether instead of 2-chloroethyl methylsulfide, a reaction was carried out to obtain 3.71 g. of 4-(2-n-butoxyethoxy)-N-(2-3,-dichlorophenyl)-benzamide having a melting point of 70° to 72° C. as the object product. The yield was 48.6%.

Preparation No. 7: (Compound No. 13)

In accordance with the process of Preparation 3, except using 5.07 g. of 2-bromoethyl ethylsulfide instead of 2-chloroethyl methylsulfide, a reaction was carried out to obtain 5.85 g. of 4-(2-ethylthioethoxy)-N-(2,3-dichlorophenyl)-benzamide having a melting point of 111° to 112° C. as the object product. The yield was 79.0%.

Preparation No. 8: (Compound No. 2)

Into 50 ml. of N,N-dimethylformamide, 6.4 g. of potassium 4-hydroxy-N-(2,3-dichlorophenyl)-benzamide was dispersed and then, 3.8 g. of chloromethyl ethyl ether was added dropwise at 0° C. during 30 minutes. After the addition at the same temperature during 30 minutes, the mixture was stirred at room temperature for 30 minutes. After the reaction, the solvent was recovered by a rotary evaporator. The resulting residue was dissolved into 100 ml. of toluene and the solution was washed for 2 times with 100 ml. of water and dehydrated over anhydrous sodium sulfate and toluene was recovered by a rotary evaporator to obtain an oily product. The oily product was crystallized from methanol to obtain 4.2 g. of 4-ethoxymethoxy-N-(2,3-dichlorophenyl)-benzamide as the object product. The yield was 61.7%. The compound had a melting point of 87.0° to 88.5° C.

Preparation No. 9: (Compound No. 1)

In accordance with the process of Preparation 8, except using 3.22 g. of chloromethyl methyl ether instead of chloromethyl ethyl ether, a reaction was carried out to obtain 3.32 g. of 4-methoxy-methoxy-N-(2,3-dichlorophenyl)-benzamide having a melting point of 109° to 111° C. as the object product. The yield was 50.8%.

Preparation No. 10: (Compound No. 3)

In accordance with the process of Preparation 8, except using 4.38 g. of chloromethyl n-propyl ether instead of chloromethyl ethyl ether, a reaction was carried out to obtain 4.19 g. of 4-n-propoxymethoxy-N-(2,3-dichlorophenyl)-benzamide having a melting point of 68.5° to 70.5° C. as the object product. The yield was 59.2%.

Preparation No. 11: (Compound No. 9)

In accordance with the process of Preparation 8, except using 3.86 g. of chloromethyl methylsulfide instead of chloromethyl ethyl ether, a reaction was carried out to obtain 3.80 g. of 4-methylthiomethoxy-N-(2,3-dichlorophenyl)-benzamide having a melting point of 113° to 115° C. as the object product. The yield was 55.5%.

Preparation No. 12: (Compound No. 10)

In accordance with the process of Preparation 8, except using 3.32 g. of chloromethyl ethylsulfide instead of chloromethyl ethyl ether, a reaction was carried out to obtain 4.85 g. of 4-ethylthiomethoxy-N-(2,3-dichlorophenyl)-benzamide having a melting point of 89.5° to 91.0° C. as the object product. The yield was 68.1%.

Preparation No. 13: (Compound No. 11)

In accordance with the process of Preparation 8, except using 4.16 g. of n-butyl chloromethylsulfide instead of chloromethyl ethyl ether, a reaction was carried out to obtain 5.90 g. of 4-n-butylthiomethoxy-N-(2,3-dichlorophenyl)-benzamide having a melting point of 58.5° to 60.5° C. as the object product. The yield was 76.8%.

Preparation No. 14: (Compound No. 5)

In accordance with the process of Preparation 8, except using 5.56 g. of 2-bromoethyl methyl ether instead of chloromethyl ethyl ether, a reaction was carried out to obtain 4.89 g. of the object compound of 4-(2-methoxyethoxy)-N-(2,3-dichlorophenyl)-benzamide. The yield was 71.9%.

The herbicidal compositions of the present invention can be obtained by admixing the active ingredient with a desired adjuvant so as to form a wettable powder, an emulsifiable concentrate, a dust, a granule etc.

The liquid adjuvant is usually an organic solvent and the solid adjuvant is usually mineral fine powder. In order to impart emulsifiable property, dispersable property and spreadable property, a desired surface active ingredient is added. The active ingredient can be used by admixing with an agricultural chemical such as a fertilizer, a herbicide, an insecticide and a germicide.

The active ingredient of the compound of the present invention is applied depending upon a weather condition, a soil condition, a form of the composition, a season of the application and a method of the application and kinds of crop plants and kinds of weeds. The active ingredient is usually applied in a range of 1 to 2,000 g. preferably 1 to 1,000 g., especially 100 to 500 g. per 10 are in the treatment. The active ingredient is usually used in the form of a wettable powder, an emulsifiable concentrate or, a dust or a granule which comprises 0.1 to 50 wt.% of the active ingredient. The active ingredient is usually applied in a concentration of 10 to 10,000 ppm preferably 100 to 5,000 ppm. especially 250 to 3,000 ppm. of the active ingredient.

In the preparation of the emulsifiable concentrate, the active ingredient is dissolved in an agricultural acceptable organic solvent and a solvent soluble emulsifier is added. Suitable solvent is not usually miscible to water and include organic solvents such as hydrocarbons, chlorinated hydrocarbons, ketones, esters, alcohols and amides. Suitable solvents include toluene, xylene, naphtha, perchloroethylene, cyclohexanone, isophorone, dimethylformamide and mixtures thereof. The optimum solvents include aromatic hydrocarbons and ketones. A mixture of solvents is usually used. The surfactants used as the emulsifier is incorporated at a ratio of 0.5 to 20 wt.% based on the emulsifiable concentrate. The surfactants can be anionic, cationic or nonionic surfactants. Suitable anionic surfactants include higher alcholsulfates or sulfonates, alkylarylsulfonates or sulfosuccinates, such as calcium dodecylbenzenesulfonate and sodium dioctylsulfosuccinate etc. Suitable cationic surfactants include aliphatic alkylamines and aliphatic acid alkyl quaternary salts such as laurylamine hydrochloride and lauryldimethylbenzylammonium chloride. Suitable nonionic surfactants include ethylene oxide adducts of alkylphenol, aliphatic alcohol, mercaptane or aliphatic acid such as polyethyleneglycol ester of stearic acid or polyethyleneglycol ethers of palmityl alcohol or octylphenol.

The concentration of the active ingredient is in a range of 0.5 to 80 wt.% especially 5 to 40 wt.%.

The wettable powder is prepared by incorporating the active ingredient in an inert fine powder and a surfactant. The active ingredient is usually incorporated at a ratio of 1 to 50 wt.% and the surfactant is incorporated at a ratio of 0.5 to 20 wt.%. The solid carriers usually used with the active ingredient include natural products of clay, silicates, silica, lime and carbonates and organic carriers. Suitable carriers include kaolin, jeeklite, fuller's earth talc, diatomaceous earth, magnesium lime, dolomite, and walnut shell powder.

The emulsifiers and wetting agents used in the wettable powder include polyoxyethylene-alkylphenols, aliphatic alcohols or aliphatic acids and alkylamines, alkylarylsulfonates, and dialkylsulfosuccinates. Suitable spreaders include glycerin mannitol laurate and condensates of oleic acid and polyglycerin modified with phthalic anhydride. Suitable dispersing agents include condensates of maleic anhydride and olefin such as sodium salt of copolymer of diisobutylene and maleic acid; sodium ligninsulfonate; and sodium formaldehydenaphthalenesulfonate, etc. The dust is prepared by incorporating the active ingredient in an inert carrier used for dusts such as talc, fine clay, agalmatolite, diatomaceous earth, magnesium carbonate or wheat powder.

A concentrated dust containing the active ingredient of 10 to 80 wt.% is usually prepared. In the application as a herbicide, it is diluted with a solid carrier at a concentration of about 1 to 20 wt.%.

The granule is prepared by incorporating the active ingredient in a granular or pelletized agricultural acceptable carrier such as bentonite, kaolin clay, diatomaceous earth and talc having particle size of 8 to 60 mesh. The granule contains 1 to 50 wt.% of the active ingredient.

The amounts of the active ingredients, adjuvants and additives in the herbicidal compositions of the present invention will be further illustrated.

Emulsifiable concentrate:
Active ingredient: 0.5 to 80 wt.% preferably 5 to 40 wt.%
Surfactant: 1 to 40 wt.% preferably 5 to 20 wt.%
Liquid carrier: 5 to 95 wt.% preferably 50 to 90 wt.%

Wettable powder:
Active ingredient: 1 to 50 wt.% preferably 5 to 30 wt.%
Surfactant: 0.5 to 20 wt.% preferably 1 to 10 wt.%
Solid carrier: 5 to 99 wt.% preferably 50 to 95 wt.%

Granule:
Active ingredient: 0.5 to 50 wt.% preferably 1 to 20 wt.%
Solid carrier: 50 to 98.5 wt.% preferably 70 to 90 wt.%
Surfactant: 1 to 10 wt.% preferably 2 to 5 wt.%

Dust:
Active ingredient: 0.5 to 10 wt.% preferably 1 to 5 wt.%
Solid carrier: 90 to 99.5 wt.% preferably 95 to 99 wt.%

The herbicidal compositions of the present invention mainly suppress seadling and growth of weeds. The herbicidal compositions impart excellent herbicidal effect for gramineous weeds of barnyard grass, marsh grass, sprangletop and monochoria by a soil treatment in a flooded condition. Moreover, the herbicidal compositions impart growth control effect to broad leaf weeds such as long stemmed waterwort and toothcup. No phytotoxicity to transplanted rice seedling is not found. Thus, the herbicidal composition has high selectivity.

The herbicidal compositions of the present invention will be illustrated by certain examples.

EXAMPLE 1: (Wettable Powder)

Jeeklite: 97 wt. parts
Neopelex powder (Kao-Atlas Co.): 1.5 wt. parts
Sorpol 800 A (Toho Kagaku Kogyo): 1.5 wt. parts These components were uniformly pulverized and mixed to prepare a carrier for wettable powder.

The resulting carrier for wettable powder (90 wt. parts) and Active ingredient (Compound No. 2) (10 wt. parts) were uniformly pulverized and mixed to obtain a wettable powder.

EXAMPLE 2: (Emulsifiable concentrate)

Active ingredient (Compound No. 4): 10 wt. parts
Cyclohexanone: 40 wt. parts
Xylene: 40 wt. parts
Sorpol 800 A (Toho Kagaku Kogyo): 10 wt. parts The components were uniformly mixed to obtain an emulsifiable concentrated.

EXAMPLE 3: (Granule)

Active ingredient (Compound No. 10): 7 wt. parts
Bentonite: 44 wt. parts
Kaolin clay: 44 wt. parts
Sodium ligninsulfonate: 5 wt. parts The components were uniformly mixed and water was added and the mixture was kneaded, granulated and dried to obtain a granule.

EXAMPLE 4: (Wettable powder)

Active ingredient (Compound No. 2): 50 wt. parts
Kaolin clay: 45 wt. parts
Sorpol 5039 (Toho Kagaku Kogyo): 5 wt. parts These components were uniformly mixed to obtain a wettable powder.

EXAMPLE 5: (Emulsifiable concentrate)

Active ingredient (Compound No. 4): 25 wt. parts
Xylene: 35 wt. parts
Cyclohexanone: 30 wt. parts
Sorpol 800 A (Toho Kagaku Kogyo): 10 wt. parts These components were uniformly mixed to obtain an emulsifiable concentrate.

Test 1:

Each porcelain pot of 1/15,500 are was filled with paddy soil and seeds of barnyard grass, marsh grass, sprangletop were uniformly sown on the surface layer, and flooded in a depth of 2 cm. Two seedlings of rice (species: Nihon bare) at two leaf stage were transplanted. At the time of germination of the weeds, each diluted solution of a wettable powder containing each active ingredient was poured into water at each dose of the active ingredient. Twenty days after the treatment with the active ingredient, the herbicidal effect to barnyard grass, marsh grass, sprangletop and the phytotoxicity to the transplanted rice seedlings were observed. The test results are shown by the following ratings.

| Herbicidal effect | Phytotoxicity to transplanted rice seedling |
|---|---|
| 0: none | −: none phytotoxicity |
| 1: growth suppression of 20–30% | ±: substantial none-phytotoxicity |
| 2: growth suppression of 40–50% | +: slight damage |
| 3: growth suppression of 60–70% | ++: damage |
| 4: growth suppression of 80–90% | +++: remarkable damage |
| 5: complete growth suppression | |

The test results are shown in Table 2.

As shown in Table 2, the compounds of the present invention had remarkably high herbicidal effect to remarkably high herbicidal effect to the gramineous weeds of barnyard grass, marsh grass and sprangletop without any phytotoxicity to the transplanted rice plant as the gramineous crop plant.

TABLE 2

| Comp. No. | Dose g./10 are | Phytotoxicity of rice seedling | Herbicidal effect | | |
|---|---|---|---|---|---|
| | | | Barnyard grass | Marsh grass | Sprangletop |
| 1 | 1000 | — | 5 | 5 | 5 |
|   | 500  | — | 5 | 5 | 5 |
|   | 250  | — | 4.5 | 4.5 | 4.5 |
|   | 125  | — | 4 | 4 | 4 |
|   | 62.5 | — | 2 | 1 | 1 |
| 2 | 1000 | — | 5 | 5 | 5 |
|   | 500  | — | 5 | 5 | 5 |
|   | 250  | — | 5 | 5 | 5 |

TABLE 2-continued

| Comp. No. | Dose g./10 are | Phyto-toxicity of rice seedling | Herbicidal effect Barnyard grass | Marsh grass | Sprangle-top |
|---|---|---|---|---|---|
|  | 125 | — | 5 | 5 | 5 |
|  | 62.5 | — | 5 | 5 | 5 |
| 3 | 1000 | — | 5 | 5 | 5 |
|  | 500 | — | 5 | 5 | 5 |
|  | 250 | — | 5 | 4.5 | 5 |
|  | 125 | — | 4.5 | 4 | 4.5 |
|  | 62.5 | — | 4.5 | 4 | 4 |
| 4 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 5 | 5 | 5 |
| 5 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 2 | 3 | 2 |
| 6 | 1000 | ± | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 3 | 2 | 3 |
| 7 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 1 | 1 | 2 |
| 8 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 1 | 1 | 1 |
| 9 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 4 | 3 | 4 |
| 10 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 5 | 4.5 | 4.5 |
| 11 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 4 | 4 | 4 |
| 12 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 4 | 4 | 4.5 |
| 13 | 1000 | — | 5 | 5 | 5 |
|  | 500 | — | 5 | 5 | 5 |
|  | 250 | — | 5 | 5 | 5 |
|  | 125 | — | 5 | 5 | 5 |
|  | 62.5 | — | 4 | 4.5 | 4 |

Test 2:

Each porcelain pot of 1/15,500 are was filled with paddy soil and seeds of barnyard grass and sprangletop were uniformly sown on the surface layer, and flooded in a depth of 2 cm. Two seedlings of rice (species: Nihon bare) at two leaf stage were transplanted. Five days or ten days after the transplantation, each diluted solution of each emulsifiable concentrate was added dropwise by a pipet at a specific dose of the active ingredient.

Twenty days after the treatment with the active ingredient, the herbicidal effect and the phytotoxicity to the transplanted rice seedlings were observed. The test results are shown in Table 3.

The rating is the same as that of Test 1.

As shown in Table 3, the compounds of the present invention in the emulsifiable concentrate had remarkably high herbicidal effect to the gramineous weeds of barnyard grass and sprangletop without any phytotoxicity to the transplanted rice plant as the gramineous crop plant.

TABLE 3

| Comp. No. | Dose g./10 are | Treatment 5 days after transplantation | | | Treatment 10 days after transplantation | | |
|---|---|---|---|---|---|---|---|
| | | Herbicidal effect | | Phyto-toxicity to rice | Herbicidal effect | | Phyto-toxicity to rice |
| | | Barnyard grass | Sprangletop | | Barnyard grass | Sprangletop | |
| 1 | 800 | 5 | 5 | — | 5 | 5 | — |
|  | 400 | 5 | 5 | — | 5 | 5 | — |
|  | 200 | 4 | 4 | — | 4 | 3 | — |
|  | 100 | 3 | 3 | — | 3 | 2 | — |
| 2 | 800 | 5 | 5 | — | 5 | 5 | — |
|  | 400 | 5 | 5 | — | 5 | 5 | — |
|  | 200 | 5 | 5 | — | 5 | 5 | — |
|  | 100 | 5 | 5 | — | 5 | 5 | — |
| 3 | 800 | 5 | 5 | — | 5 | 5 | — |
|  | 400 | 5 | 5 | — | 5 | 5 | — |
|  | 200 | 5 | 5 | — | 5 | 5 | — |
|  | 100 | 5 | 5 | — | 5 | 5 | — |
| 5 | 800 | 5 | 5 | — | 5 | 5 | — |
|  | 400 | 5 | 5 | — | 5 | 5 | — |
|  | 200 | 5 | 5 | — | 5 | 5 | — |
|  | 100 | 5 | 4.5 | — | 5 | 4 | — |
| 6 | 800 | 5 | 5 | — | 5 | 5 | — |
|  | 400 | 5 | 5 | — | 5 | 5 | — |
|  | 200 | 5 | 5 | — | 5 | 5 | — |
|  | 100 | 4.5 | 4.5 | — | 4.5 | 4 | — |
| 8 | 800 | 5 | 5 | — | 5 | 5 | — |
|  | 400 | 5 | 5 | — | 5 | 5 | — |
|  | 200 | 5 | 5 | — | 5 | 5 | — |
|  | 100 | 4 | 3 | — | 4 | 2 | — |
| 10 | 800 | 5 | 5 | — | 5 | 5 | — |

TABLE 3-continued

| Comp. No. | Dose g./10 are | Treatment 5 days after transplantation | | | Treatment 10 days after transplantation | | |
|---|---|---|---|---|---|---|---|
| | | Herbicidal effect | | | Herbicidal effect | | |
| | | Barnyard grass | Sprangletop | Phytotoxicity to rice | Barnyard grass | Sprangletop | Phytotoxicity to rice |
| | 400 | 5 | 5 | — | 5 | 5 | — |
| | 200 | 5 | 5 | — | 5 | 5 | — |
| | 100 | 5 | 5 | — | 5 | 5 | — |
| 12 | 800 | 5 | 5 | — | 5 | 5 | — |
| | 400 | 5 | 5 | — | 5 | 5 | — |
| | 200 | 5 | 5 | — | 5 | 5 | — |
| | 100 | 5 | 4.5 | — | 5 | 4 | — |

Test 3:

Each wagner pot of 1/5,000 are was filled with paddy soil and a paddy soil containing weeds of barnyard grass and sprangletop was covered as a surface layer and it was treated by a manuring an irrigation and a puddling and it was flooded in a depth of 4 cm. Three seedlings of two stands rice (species: Nihon bare) at 2.5 leaf stage were transplanted. Three days or seven days after the transplantation, each granule of each active ingredient prepared by Example 3 was applied at each specific dose of each active ingredient.

Twenty days after the treatment with the active ingredient, the herbicidal effect and the phytotoxicity to the transplanted rice seedlings were observed. The test results are shown in Table 4. The rating is the same as that of Test 1.

As shown in Table 4, the compounds of the present invention in the granular form had remarkably high herbicidal effect without any phytotoxicity to rice seedlings.

We claim:

1. Benzamide derivatives having the formula

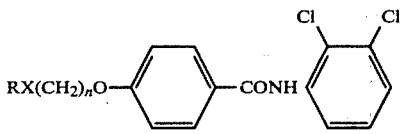

wherein R represents a $C_1$-$C_8$ alkyl group; X represents oxygen or sulfur atom; n is an integer of 1 or 2.

2. Benzamide derivatives having the formula:

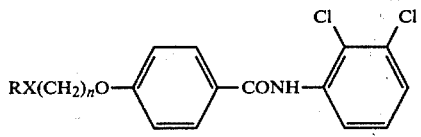

TABLE 4

| Comp. No. | Dose g./10 are | Treatment 3 days after transplantation | | | Treatment 7 days after transplantation | | |
|---|---|---|---|---|---|---|---|
| | | Herbicidal effect | | | Herbicidal effect | | |
| | | Barnyard grass | Sprangletop | Phytotoxicity to rice | Barnyard grass | Sprangletop | Phytotoxicity to rice |
| 1 | 420 | 5 | 5 | — | 5 | 5 | — |
| | 280 | 5 | 5 | — | 5 | 5 | — |
| | 140 | 4 | 4 | — | 4 | 3.5 | — |
| 2 | 420 | 5 | 5 | — | 5 | 5 | — |
| | 280 | 5 | 5 | — | 5 | 5 | — |
| | 140 | 5 | 5 | — | 5 | 5 | — |
| 4 | 420 | 5 | 5 | — | 5 | 5 | — |
| | 280 | 5 | 5 | — | 5 | 5 | — |
| | 140 | 5 | 5 | — | 5 | 5 | — |
| 5 | 420 | 5 | 5 | — | 5 | 5 | — |
| | 280 | 5 | 5 | — | 5 | 5 | — |
| | 140 | 5 | 5 | — | 5 | 5 | — |
| 6 | 420 | 5 | 5 | — | 5 | 5 | — |
| | 280 | 5 | 5 | — | 5 | 5 | — |
| | 140 | 5 | 5 | — | 5 | 5 | — |
| 8 | 420 | 5 | 5 | — | 5 | 5 | — |
| | 280 | 5 | 5 | — | 5 | 5 | — |
| | 140 | 5 | 5 | — | 4.5 | 5 | — |
| 9 | 420 | 5 | 5 | — | 5 | 5 | — |
| | 280 | 5 | 5 | — | 5 | 5 | — |
| | 140 | 5 | 5 | — | 5 | 5 | — |
| 10 | 420 | 5 | 5 | — | 5 | 5 | — |
| | 280 | 5 | 5 | — | 5 | 5 | — |
| | 140 | 5 | 5 | — | 5 | 5 | — |
| 11 | 420 | 5 | 5 | — | 5 | 5 | — |
| | 280 | 5 | 5 | — | 5 | 5 | — |
| | 140 | 5 | 5 | — | 5 | 5 | — |
| 13 | 420 | 5 | 5 | — | 5 | 5 | — |
| | 280 | 5 | 5 | — | 5 | 5 | — |
| | 140 | 5 | 5 | — | 5 | 5 | — | wherein R represents a $C_1$–$C_8$ alkyl group; X represents sulfur; n is an integer of 1 or 2.

3. A herbicidal composition which comprises a benzamide derivative having the formula

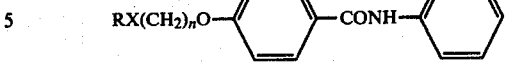

wherein R represents a $C_1$–$C_8$ alkyl group; X represents oxygen or sulfur atom; n is an integer of 1 or 2 as an active ingredient with an adjuvant.

4. A herbicidal composition according to claim 3 which comprises 0.1 to 50 wt.% of the active ingredient and 99.9 to 50 wt.% of an adjuvant.

* * * * *